United States Patent
Kozyuk et al.

(10) Patent No.: US 7,314,516 B2
(45) Date of Patent: *Jan. 1, 2008

(54) HYDRODYNAMIC CAVITATION CRYSTALLIZATION DEVICE AND PROCESS

(75) Inventors: Oleg V. Kozyuk, North Ridgeville, OH (US); Allan S. Myerson, Chicago, IL (US); Roger Weinberg, Akron, OH (US)

(73) Assignees: Five Star Technologies, Inc., Cleveland, OH (US); Illinois Institute of Technology, Chicago, IL (US)

( * ) Notice: Subject to any disclaimer, the term of this patent is extended or adjusted under 35 U.S.C. 154(b) by 341 days.

This patent is subject to a terminal disclaimer.

(21) Appl. No.: 11/025,560

(22) Filed: Dec. 29, 2004

(65) Prior Publication Data

US 2006/0137598 A1    Jun. 29, 2006

(51) Int. Cl.
    *C30B 29/58*    (2006.01)
(52) U.S. Cl. .............................. 117/68; 117/69; 117/70; 117/925; 117/927; 422/245.1
(58) Field of Classification Search .................. 117/68, 117/69, 70, 925, 927; 422/245.1
    See application file for complete search history.

(56) References Cited

U.S. PATENT DOCUMENTS

| 5,314,506 | A | 5/1994 | Midler, Jr. et al. |
| 6,302,958 | B1 | 10/2001 | Lindrud et al. |
| 6,482,438 | B1 | 11/2002 | Singh et al. |
| 6,558,435 | B2 | 5/2003 | Am Ende et al. |
| 6,607,784 | B2 | 8/2003 | Kipp et al. |
| 2002/0193254 | A1* | 12/2002 | Moser et al. ............... 505/100 |
| 2004/0173139 | A1* | 9/2004 | Kozyuk ....................... 117/2 |
| 2006/0118034 | A1* | 6/2006 | Kozyuk ....................... 117/2 |

* cited by examiner

*Primary Examiner*—Robert Kunemund
(74) *Attorney, Agent, or Firm*—Benesch, Friedlander, Coplan & Aronoff LLP

(57) ABSTRACT

A device and process for crystallizing a compound using hydrodynamic cavitation comprising the steps of mixing at least one stream of a feed solution of such compound to be crystallized with at least one stream of an anti-solvent in a nucleating section via collision of the feed solution and the anti-solvent, passing the mixed streams at an elevated pressure through at least one local constriction of flow to create hydrodynamic cavitation thereby causing nucleation and the production of seed crystals, passing the fluid stream containing the seed crystals through an intermediate section to a crystal growth section, passing the fluid stream containing the seed crystals through the crystal growth section at an elevated pressure through at least one local constriction of flow to create hydrodynamic cavitation thereby causing further crystallization of the compound contained in the solution.

21 Claims, 8 Drawing Sheets

HYDRODYNAMIC CAVITATION CRYSTALLIZATION DEVICE AND PROCESS

BACKGROUND OF THE INVENTION

The present invention relates to a device and process for crystallizing compounds using hydrodynamic cavitation. The types of compounds that may be crystallized include pharmaceutical compounds, chemical compounds, food additive compounds, as well as any other compounds used in industry.

Crystallization from solution is a separation and purification method used in the chemical, food and pharmaceutically industries, particularly for the production of active compounds or their intermediates. Some of the goals of the crystallization process include producing a product meeting the desired purity level and also a product having the desired crystal size and size distribution. Crystallization from solution is usually conducted as a batch process or as a continuous process. Batch crystallization equipment and operation is fairly simple but requires a significant investment of both time and money between batches. Additionally, batch crystallization suffers from quality control issues due to the lack of a steady state during the batch crystallization process. Continuous crystallization can involve a single. crystallizer or a series of crystallizers operating at a steady state. However, continuous crystallization is normally used for large volume commodity type materials as continuous crystallization does not typically permit adequate quality control to yield crystals suitable for use in industries demanding a high level of crystal size and size distribution control.

High bioavailability and short dissolution time are desirable or often necessary attributes of a pharmaceutical end product. However, the direct crystallization of small sized, high surface area particles is usually accomplished in a high supersaturation environment which often results in material of low purity, high friability, and decreased stability due to poor crystal structure formation. Because the bonding forces in organic crystal lattices generate a much higher frequency of amorphism than those found in highly ionic inorganic solids, "oiling out" of supersaturated material is not uncommon, and such oils often solidify without structure.

Slow crystallization is a common technique used to increase product purity and produce a more stable crystal structure, but it is a process that decreases crystallizer productivity and produces large, low surface area particles that require subsequent high intensity milling. Currently, pharmaceutical compounds almost always require a post-crystallization milling step to increase particle surface area and thereby improve their bioavailability. However, high energy milling has drawbacks. Milling may result in yield loss, noise and dusting, as well as unwanted personnel exposure to highly potent pharmaceutical compounds. Also, stresses generated on crystal surfaces during milling can adversely affect labile compounds. Overall, the three most desirable end-product goals of high surface area, high chemical purity, and high stability cannot be optimized simultaneously using current crystallization technology without high energy milling.

One standard crystallization procedure involves contacting a supersaturated solution of the compound to be crystallized with an appropriate "anti-solvent" in a stirred vessel. Within the stirred vessel, the anti-solvent initiates primary nucleation which leads to crystal formation, sometimes with the help of seeding, and crystal digestion during an aging step. Mixing within the vessel can be achieved with a variety of agitators (e.g., Rushton or Pitched blade turbines, Intermig, etc.), and the process is done in a batchwise fashion.

When using current reverse addition technology for direct small particle crystallization, a concentration gradient can not be avoided during initial crystal formation because the introduction of feed solution to anti-solvent in the stirred vessel does not afford a thorough mixing of the two fluids prior to crystal formation. The existence of concentration gradients, and therefore a heterogeneous fluid environment at the point of initial crystal formation, impedes optimum crystal structure formation and increases impurity entrainment. If a slow crystallization technique is employed, more thorough mixing of the fluids can be attained prior to crystal formation which will improve crystal structure and purity, but the crystals produced will be large and milling will be necessary to meet bioavailability requirements.

Another standard crystallization procedure employs temperature variation of a solution of the material to be crystallized in order to bring the solution to its supersaturation point, but this is a slow process that produces large crystals. Also, despite the elimination of a solvent gradient with this procedure, the resulting crystal characteristics of size, purity and stability are difficult to control and are inconsistent from batch to batch.

Another standard crystallization procedure involves contacting a supersaturated solution of the compound to be crystallized with an appropriate acid or base in a stirred vessel. This in turn causes a pH change in the supersaturated solution, thereby initiating primary nucleation and, eventually, crystal formation. Alternatively, crystallization can also be accomplished by reactive crystallization. In reactive crystallization, a reactive agent is added to a supersaturated solution, resulting in primary nucleation and, eventually, crystal formation. Similar to other standard crystallization processes, reactive crystallization is mixing dependent.

Another crystallization procedure utilizes impinging jets to achieve high intensity micromixing in the crystallization process. High intensity micromixing is a well known technique where mixing-dependent reactions are involved. In U.S. Pat. No. 5,314,456 there is described a method using two impinging jets to achieve uniform particles. The general process involves two impinging liquid jets positioned within a well stirred flask to achieve high intensity micromixing. At the point where the two jets strike one another a very high level of supersaturation exists. As a result of this high supersaturation, crystallization occurs extremely rapidly within the small mixing volume at the impingement point of the two liquids. Since new crystals are constantly nucleating at the impingement point, a very large number of crystals are produced. As a result of the large number of crystals formed, the average size remains small, although not all the crystals formed are small in size.

BRIEF DESCRIPTION OF THE DRAWINGS

These and other features, aspects, and advantages of the present invention will become better understood with regard to the following description, appended claims, and accompanying drawings where:

DETAILED DESCRIPTION OF THE INVENTION

Figure 1:
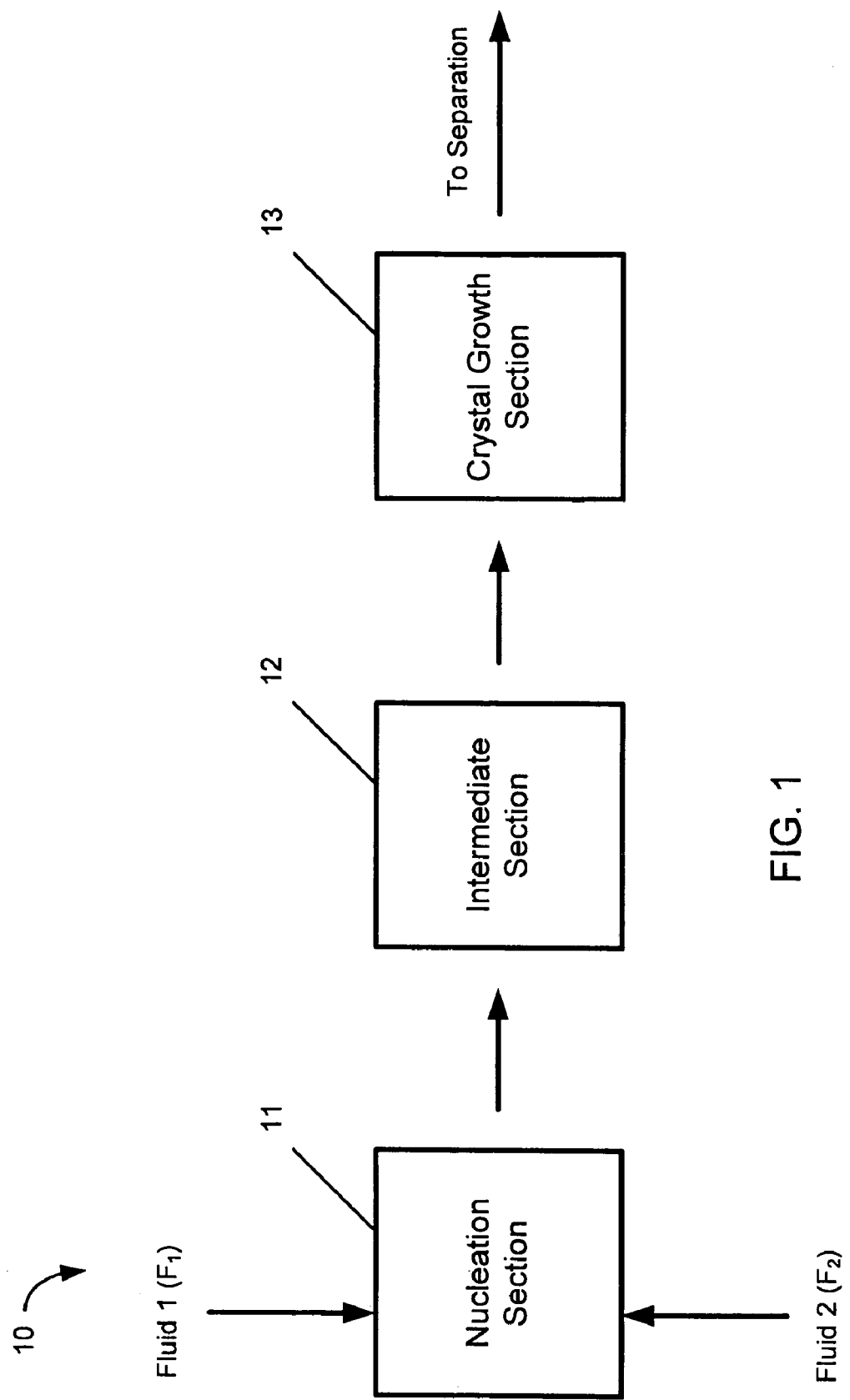
FIG. 1 is flow chart diagram of a crystallization device according to the present invention.

In the description that follows, like parts are indicated throughout the specification and drawings with the same reference numerals, respectively. The figures are not drawn to scale and the proportions of certain parts have been exaggerated for convenience of illustration.

The subject application provides a device and process for using hydrodynamic cavitation to crystallize a substance from solution. Referring now to the drawings, FIG. 1 is a flow chart diagram of one embodiment of a crystallization device 10. The crystallization device 10 includes a nucleation section 11 connected to an intermediate section 12, which is in turn connected to a crystal growth section 13. After the solution has been processed in each of the three sections of device 10, the resulting product is then separated to recover the desired crystallized product.

In one embodiment, the crystallization process is accomplished by charging at least two fluids to nucleation section 11 of device 10 to effect nucleation in a crystallization process. The two fluids used in this process can be of different solvent composition, one fluid being a solution of the compound to be crystallized in a suitable solvent or combination of solvents ("feed solution"), and the other fluid being a suitable solvent or combination of solvents capable of initiating that compound's precipitation from solution ("anti-solvent"), chosen for its relatively low salvation property with respect to that compound. Such solvents and anti-solvents can include, but are not limited to, alcohols, ethyl acetate, halogenated solvents, acids, bases, acetonitrile, hexanes, ethers, and water. Suitable examples of solvents and anti-solvents include, but are not limited to, ethanol, methanol, ethyl acetate, methylene chloride, acetonitrile, acetic acid, hexane, ether, and water. Alternatively, the anti-solvent can contain a suitable reactant compound that reacts with the compound to be crystallized in the feed solution. Given the compound to be crystallized by a reactant crystallization process, one of ordinary skill in the art would be able to select suitable reactant compounds to initiate the crystallization process.

The fluids used in this process can also contain a small amount of a suitable surfactant which may alleviate agglomeration that might occur during the hydrodynamic cavitation crystallization process. The surfactant can be added as part of a premix, or it can be added through one of the entry ports discussed herein. Thus, one, several, or all of the fluids employed may contain a surfactant. Since such a surfactant may be incorporated in the crystalline compound, a surfactant should be chosen which will be innocuous to the eventual use of the crystalline compound.

In yet another embodiment, a surfactant, stabilizer or other additive that can stabilize, control and/or promote crystal growth can be added to the anti-solvent, feed solution, or the mixed fluid stream comprising the feed solution and the anti-solvent in any one or all of the nucleation section 11, the intermediate section 12, and/or the crystal growth section 13 of the present invention.

Nucleation Sections:

The following text will discuss exemplary nucleation sections 11 for use in crystallization device 10 of the present invention. Device 10 includes at least one nucleation section. If more the one nucleation section 11 is present in device 10, nucleation sections 11 are connected in series.

Figure 2:
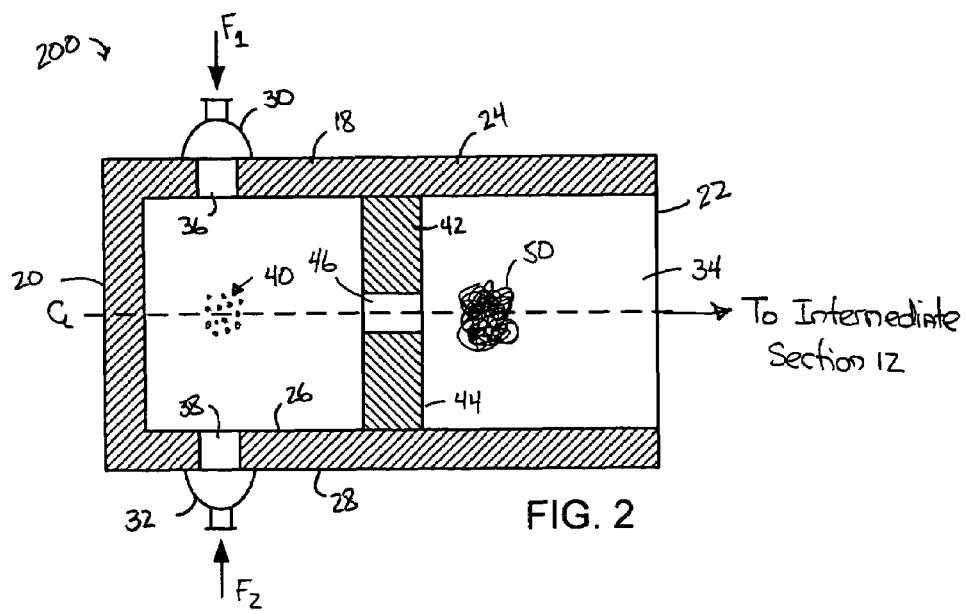
FIG. 2 is a longitudinal cross-section of hydrodynamic cavitation nucleation section 200, according to one embodiment of the present invention, that can be used in the device of FIG. 1.

Referring to FIG. 2, FIG. 2 illustrates one embodiment for a hydrodynamic cavitation nucleation section 200 that can be used as the nucleation section 11 of crystallization device 10. Hydrodynamic nucleation section 200 comprises a flow channel 18, having one seal end 20 and one open end 22. Flow channel 18 is defined by a cylindrical wall 24 having an inner surface 26, an outer surface 28, at least two ports 30 and 32 for introducing fluid streams $F_1$ and $F_2$, respectively, into section 200, and an outlet 34 for fluid to exit from section 200. Although it is preferred that the cross-section of flow channel 18 is circular, the cross-section of flow channel 18 may take the form of any geometric shape such as square, rectangular or hexagonal.

Ports 30 and 32 are connected to flow channel 18 via openings 36 and 38, respectively. Ports 30 and 32 are located in flow channel 18 opposite one another in order to permit fluid streams $F_1$ and $F_2$, respectively, to collide with one another upon entry into flow channel 18. The collision of fluid streams $F_1$ and $F_2$ creates an impingement zone 40. Bubbles are generated within impingement zone 40 as a result of fluid streams $F_1$ and $F_2$ colliding together. The creation of bubbles, the bubbles eventual collapse, and the resulting shock waves within impingement zone 40, leads to the creation of a hydrodynamic transient cavitation field within impingement zone 40. As a result, minute seed crystals are formed within impingement zone 40.

Disposed within flow channel 18 along or near the center line $C_L$ of flow channel 18 is a cavitation generator 42 configured to generate a fixed hydrodynamic cavitation field 50 downstream from cavitation generator 42. As shown in FIG. 2, cavitation generator 42 is a disk 44 having a circular orifice 46 disposed therein situated along or near the center line $C_L$ of flow channel 18. Orifice 46 is in the shape of Venturi tube and produces a local constriction of fluid flow.

To further promote the creation and control of cavitation fields downstream from disk 44 having orifice 46, disk 44 having orifice 46 is constructed to be removable and replaceable by any disk having an orifice shaped and configured in a variety of ways to generate varied hydrodynamic cavitation fields. The shape and configuration of orifice 46 can significantly affect the character of the cavitation flow and, correspondingly, the quality of nucleation. Although there are an infinite variety of shapes and configurations that can be utilized, U.S. Pat. No. 5,969,207 discloses several acceptable baffle shapes and configurations.

Figure 3:
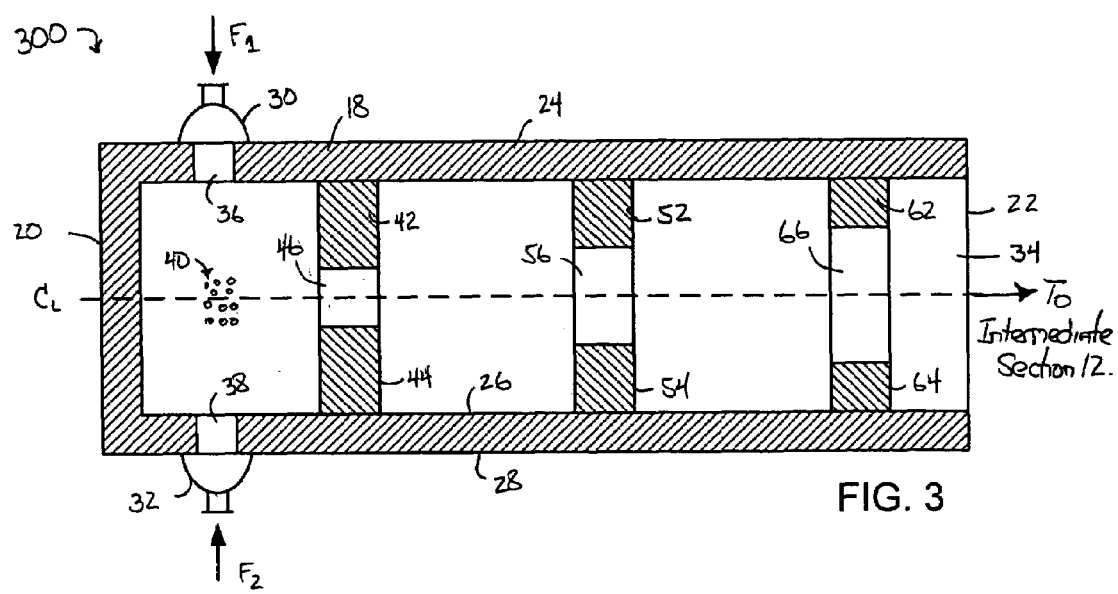
FIG. 3 is a longitudinal cross-section of hydrodynamic cavitation nucleation section 300, according to one embodiment of the present invention, that can be used in the device of FIG. 1.

In a slightly different embodiment as shown in FIG. 3, section 300 includes a multiple cavitation generators 42, 52 and 62. Cavitation generators 52 and 62 are also formed from disks 54 and 64, respectively. Cavitation generators 42, 52 and 62 each have an orifice 46, 56 and 66, respectively, therein. As with section 200, the cavitation generators of section 300 are removable and replaceable by any disk having an orifice shaped and configured in a variety of ways to generate varied hydrodynamic cavitation fields, as detailed above. First orifice 46 is in the shape of a Venturi tube and produces a local constriction of flow. Second cavitation generator 52 includes a second orifice 56, also in the shape of a Venturi tube, having a diameter that is greater than the diameter of first orifice 46. Third cavitation generator 62 includes a third orifice 66, also in the shape of a Venturi tube, having a diameter that is greater than the diameter of second orifice 56. Obviously, in another embodiment, the diameters of the first, second and third orifices may be varied as desired. In still another embodiment, the diameters of orifices 46, 56 and 66 are all the same.

In operation of section 200 illustrated in FIG. 2, first fluid stream $F_1$ enters flow channel 18 via port 30 and opening 36, second fluid stream $F_2$ enters flow channel 18 via port 32 and opening 38. Fluid streams $F_1$ and $F_2$ collide against one another, mix and generate impingement zone 40. Next, the combination of fluid streams $F_1$ and $F_2$ flows through flow channel 18 along the direction indicated by the arrow at the end of center line $C_L$. In one example, first fluid stream $F_1$ is an anti-solvent and second fluid stream $F_2$ is a feed solution. Alternatively, first fluid stream $F_1$ is a feed solution and second fluid stream $F_2$ is an anti-solvent.

The mixed first and second fluid streams $F_1$, $F_2$ then pass through orifice 46, where the velocity of first and second fluid streams $F_1$, $F_2$ increases to a minimum velocity (i.e., velocity at which cavitation bubbles begin to appear) dictated by the physical properties of the first and second fluid streams $F_1$, $F_2$. As the first and second fluid streams $F_1$, $F_2$ pass through orifice 46, fixed hydrodynamic cavitation field 50 (which generates cavitation bubbles) is formed downstream of orifice 46. Upon reaching an elevated static pressure zone, the bubbles collapse causing high local pressures (up to 5,000 kg/cm$^2$) and/or shock waves, and temperatures (up to 15,000° C.) to effect nucleation and thereby directly producing additional seed crystals. The remaining fluids and the seed crystals contained therein exit flow channel 18 via outlet 34 and are conveyed, via any suitable means (e.g., a pipe), to intermediate section 12 of device 10.

In operation of section 300 illustrated in FIG. 3, nucleation section 300 of FIG. 3 operates in a manner identical to section 200 of FIG. 2 except that mixed first and second fluid streams $F_1$, $F_2$ pass through orifices 46, 56 and 66 of cavitation generators 42, 52 and 62. Cavitation generators 42, 52 and 62 are designed to create three stages of hydrodynamic cavitation. The resulting mixed fluid and the seed—crystals formed due to the hydrodynamic cavitation are conveyed, via any suitable means (e.g., a pipe), to intermediate section 12 of device 10.

Figure 4:
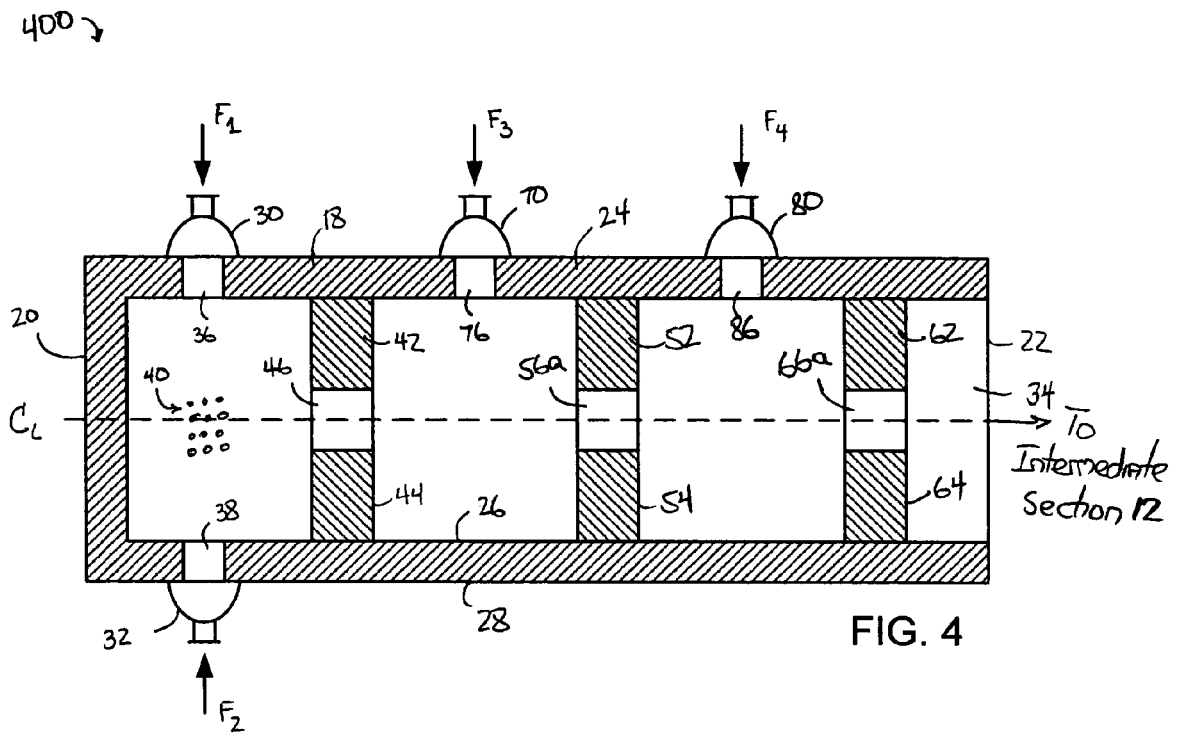
FIG. 4 is a longitudinal cross-section of hydrodynamic cavitation nucleation section 400, according to one embodiment of the present invention, that can be used in the device of FIG. 1.

FIG. 4 illustrates yet another embodiment of a hydrodynamic cavitation nucleation section 400 which is similar to section 300 illustrated in FIG. 3 in structure and operation, except section 400 has two additional entry ports, ports 70 and 80 that are connected to flow channel 18 via openings 76 and 86, respectively. Ports 70 and 80 permit the input of fluid streams $F_3$ and $F_4$ into flow channel 18. In one example, fluid streams $F_3$ and $F_4$ are both anti-solvents when fluid stream $F_1$ is an anti-solvent. In another example, fluid streams $F_3$ and $F_4$ are feed solutions when fluid stream $F_1$ is a feed solution. In still another example, fluid streams $F_3$ and $F_4$ can independently be either an anti-solvent or a feed solution regardless of the nature of fluid stream $F_1$.

Section 400 of FIG. 4 contains cavitation generators 42, 52 and 62 having orifices 46, 56 and 66, respectively. In the embodiment of FIG. 4, orifices 46, 56 and 66 are all the same diameter. In another embodiment, orifices 46, 56 and 66 can have diameters that are different from each other.

In the example where streams $F_1$, $F_3$, and $F_4$ are all anti-solvent fluid streams, the anti-solvent may be supplied continuously to nucleating section 400 to control the supersaturation properties of the fluid stream in flow channel 18.

Figure 5:
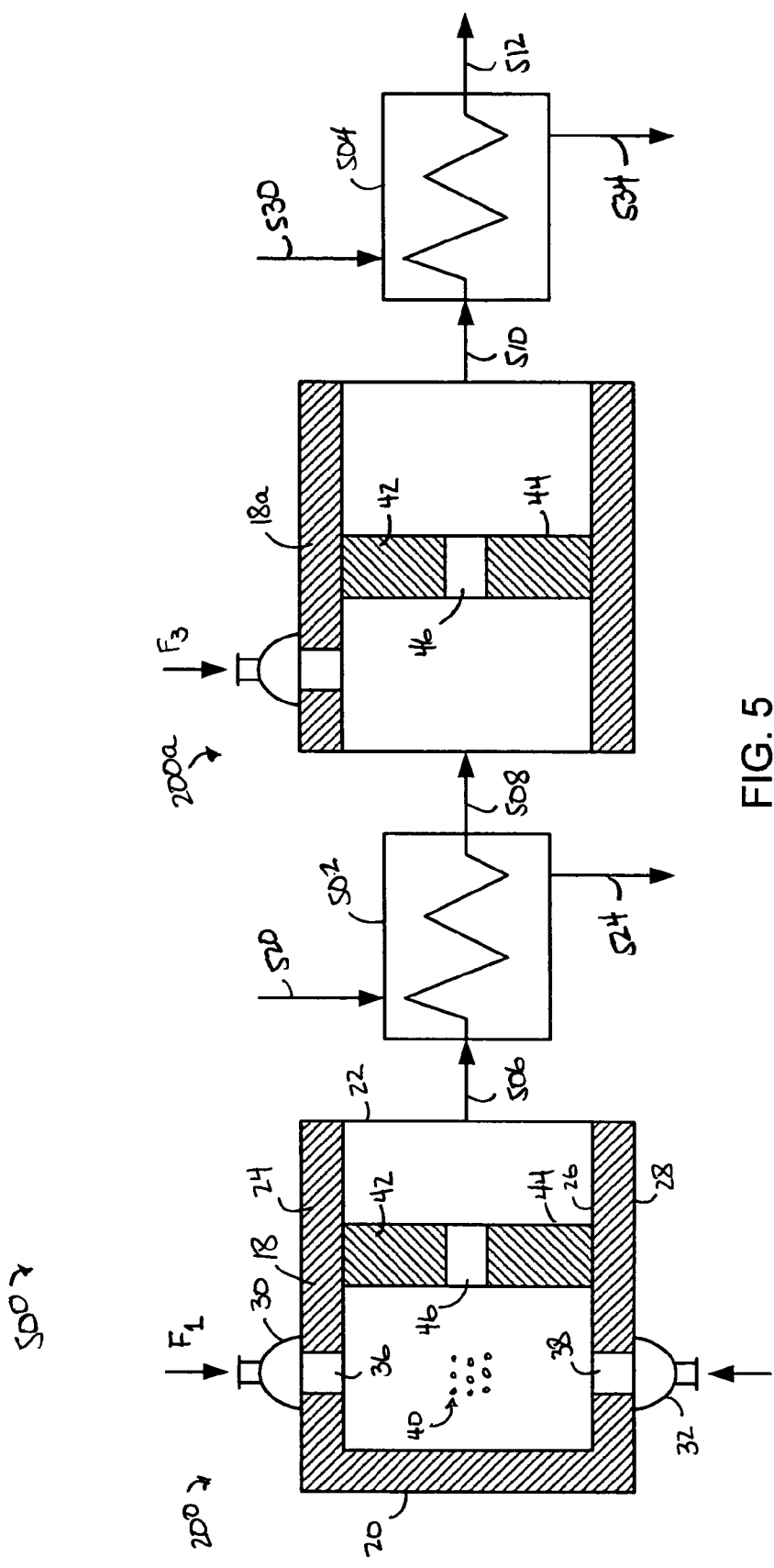
FIG. 5 is a longitudinal cross-section of hydrodynamic cavitation nucleation section 500, according to one embodiment of the present invention, that can be used in the device of FIG. 1.

Referring now to FIG. 5, a hydrodynamic cavitation nucleation section 500 comprises a closed-ended nucleation sub-section 200 and an open-ended nucleation sub-section 200a. Sub-section 200 of FIG. 5 is identical in structure and operation to nucleation section 200 of FIG. 2. Sub-section 200a of FIG. 5 differs in structure from section 200 of FIG. 2 in that flow channel 18 is a flow-through channel 18a having two open ends in sub-section 200a. Flow-through channel 18a permits the input of a pre-mixed and pre-nucleated fluid into sub-section 200a from sub-section 200. In one example, first fluid stream $F_1$ is an anti-solvent and second fluid stream $F_2$ is a feed solution. Alternatively, in another example, first fluid stream $F_1$ is a feed solution and second fluid stream $F_2$ is an anti-solvent. Third fluid stream $F_3$ can be independently selected from a feed solution or an anti-solvent.

Interposed between sub-sections 200 and 200a is a heat exchange sub-section 502. A second heat exchange sub-section 504 is placed on the output side of sub-section 200a. Sub-section 200 is connected via any suitable means 506 (e.g., a pipe) to heat exchanger 502. Heat exchanger 502 is connected via any suitable means 508 to sub-section 200a, and sub-section 200a is connected via any suitable means 510 to heat exchanger 504. Heat exchanger 504 is connected via any suitable means 512 to an intermediate section 12 of device 10.

There are a variety of heat exchangers suitable for use with a fluid stream. One such heat exchanger includes a thermally conductive pipe contained in sealed enclosure that can be filled, via any suitable means, with a cooling agent or heating agent. The cooling agent can be any gas, liquid or solid that can be used to lower the temperature of the fluid stream passing through the thermally conductive pipe of the heat exchanger. The heating agent can be any gas, liquid or solid that can be used to raise the temperature of the fluid stream passing through the thermally conductive pipe of the heat exchanger. In one embodiment, the heat exchanger has a control means (e.g., a thermostat) and related temperature control system that permits the cooling agent or heating agent to be maintained at a constant temperature.

Suitable cooling agents include any gas, liquid or solid (e.g., ice or dry ice), or even a mechanical or electrical system, that can be used to lower the temperature of a fluid stream. Examples of cooling agents include, but are not limited to, water, ice, dry ice, ethylene glycol, liquid nitrogen, and liquid helium. Suitable heating agents include any gas, liquid or solid (e.g., a sand bath), or even a mechanical or electrical system, that can be used to raise the temperature of a fluid stream. Suitable heating agents include, but are not limited to, steam, super-heated water, electric-based heaters, gas based heaters, oil, and a heated sand bath.

Depending upon whether the fluid stream passing through heat exchangers 502 and 504 is being heated or cooled, arrows 520 and 530 represent the addition of either a heating agent or a cooling agent, while arrows 524 and 534 represent the removal of the heating agent or cooling agent after the agent has undergone a temperature change as a result of coming into contact with the thermally conductive pipe carrying the fluid stream in heat exchangers 502 and 504.

Heat exchangers 502 and 504 can be designed to provide any desired temperature or temperature range necessary to facilitate nucleation, formation and/or maintenance of seed crystals in the fluid stream contained therein. Based upon the compound to be crystallized and/or the physical properties of the crystals to be produced by the described above and illustrated in the figures, one of ordinary skill in the art would recognize an appropriate temperature or temperature range for the one or more heat exchangers provided in nucleation section 500.

Regarding the embodiment illustrated in FIG. 5, sub-sections 200 and 200a can be replaced independently by any of the nucleation sections illustrated in FIGS. 2 through 4. In the case where sub-section 200a is to be replaced by a nucleation section as disclosed in FIGS. 2 through 4, the nucleation section of FIGS. 2 through 4, to be used as a replacement for sub-section 200a of FIG. 5, should be designed to be an open-ended nucleation sub-section having a flow-through channel similar to flow-through channel 18a of FIG. 5.

First, second, third and fourth fluid streams $F_1$, $F_2$, $F_3$ and $F_4$ are fed into any of the nucleating sections discussed above with the aid of a pump (not shown). The type of pump selected is determined on the basis of the physiochemical properties of the pumpable medium and the hydrodynamic parameters necessary for the accomplishment of the process.

In the nucleating sections discussed above two types of hydrodynamic cavitation fields are generated. The first type of cavitation field is a transient cavitation field generated by the collision of one fluid stream against another in an impingement zone. In the present invention the two fluid streams can be a feed solution stream and an anti-solvent stream. In another embodiment, the two solution streams can be a mixed fluid stream colliding with an additional fluid stream of feed solution or anti-solvent (see, for example, the nucleating sections of FIGS. 4 and 5). The second type of cavitation field is a fixed cavitation field generated by a controlled pressure reduction in the fluid stream caused by at least one physical flow constriction contained within the nucleating section. (Oleg—Is the collision of the mixed fluid stream with an additional input of either anti-solvent or feed solution going to create additional impingement zones in the embodiments of FIGS. 4 and 5?)

Intermediate Sections:

The following text will discuss exemplary intermediate sections 12 for use in crystallization device 10 of the present invention. Device 10 includes at least one intermediate section 12. If more than one intermediate section 12 is present in device 10, intermediate sections 12 are connected in series.

Figure 6:
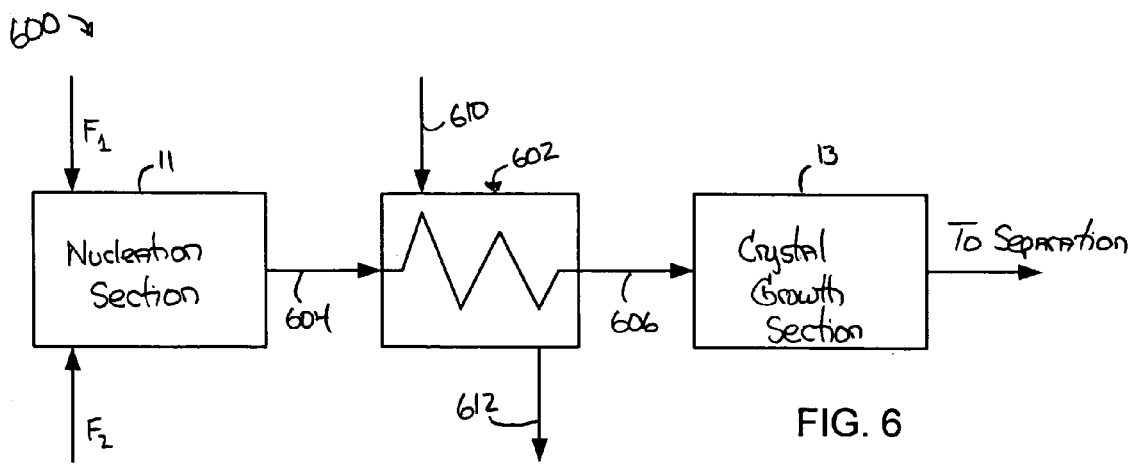
FIG. 6 is a flow diagram illustrating a crystallization device 600 according to the present invention having an intermediate section 602, according to one embodiment of the present invention, that can be used in the device of FIG. 1.

Referring now to FIG. 6, FIG. 6 illustrates one embodiment of a crystallization device 600 according to the present invention. Device 600 comprises an intermediate section 602 positioned between and connected to a nucleation section 11 and a crystal growth section 13. Intermediate section 602 is connected via any suitable connections means 604 (e.g., a pipe) to nucleation section 11, and is further connected via any suitable means 606 to crystal growth section 13. Nucleation section 11 it at least one nucleation section as disclosed in FIGS. 2 through 5 and the related text. Suitable crystal growth sections for use as section 13 will be explained in detail below.

In one embodiment, intermediate section 602 of FIG. 6 is a heat exchanger. There are a variety of heat exchangers suitable for use with a fluid stream. One such heat exchanger comprises a thermally conductive pipe contained in sealed enclosure that can be filled, via any suitable means, with a cooling agent or heating agent. The cooling agent can be any gas, liquid or solid that can be used to lower the temperature of the fluid stream passing through the thermally conductive pipe of the heat exchanger. The heating agent can be any gas, liquid or solid that can be used to raise the temperature of the fluid stream passing through the thermally conductive pipe of the heat exchanger. In one embodiment, the heat exchanger has a control means (e.g., a thermostat) and related temperature control system that permits the cooling agent or heating agent to be maintained at a constant temperature.

Suitable cooling agents include any gas, liquid or solid (e.g., ice or dry ice), or even a mechanical or electrical system, that can be used to lower the temperature of a fluid stream. Examples of cooling agents include, but are not limited to, water, ice, dry ice, ethylene glycol, liquid nitrogen, and liquid helium. Suitable heating agents include any gas, liquid or solid (e.g., a sand bath), or even a mechanical or electrical system, that can be used to raise the temperature of a fluid stream. Suitable heating agents include, but are not limited to, steam, super-heated water, electric-based heaters, gas based heaters, oil, and a heated sand bath.

Depending upon whether the fluid stream passing through heat exchanger 602 is being heated or cooled, arrow 610 represents the addition of either a heating agent or a cooling agent, while arrow 612 represents the removal of the heating agent or cooling agent after the agent has undergone a temperature change as a result of coming into contact with the thermally conductive pipe carrying the fluid stream in heat exchanger 602.

Heat exchanger 602 can be designed to provide any desired temperature or temperature range necessary to facilitate crystallization of the, compound contained in the feed solution or solutions. Based upon the compound to be crystallized and/or the physical properties of the crystals to be produced from the feed solution, one of skill in the art will recognize the appropriate temperature of temperature range in the embodiments where one or more heat exchangers are used in the nucleation section 11 of device 10.

In operation, intermediate section 602 acts as a conduit that passes the fluid stream seed crystals formed in the one or more nucleating sections to one of the crystal growth section described in further detail below. In this embodiment, intermediate section 602 also acts to maintain the desired temperature of the fluid stream and seed crystal emitted from the one or more nucleation sections described above. In another embodiment, intermediate section 602 can either increase or decrease, as desired, the temperature of the fluid stream and seed crystals emitted from the one or more nucleating sections described above.

Figure 7:
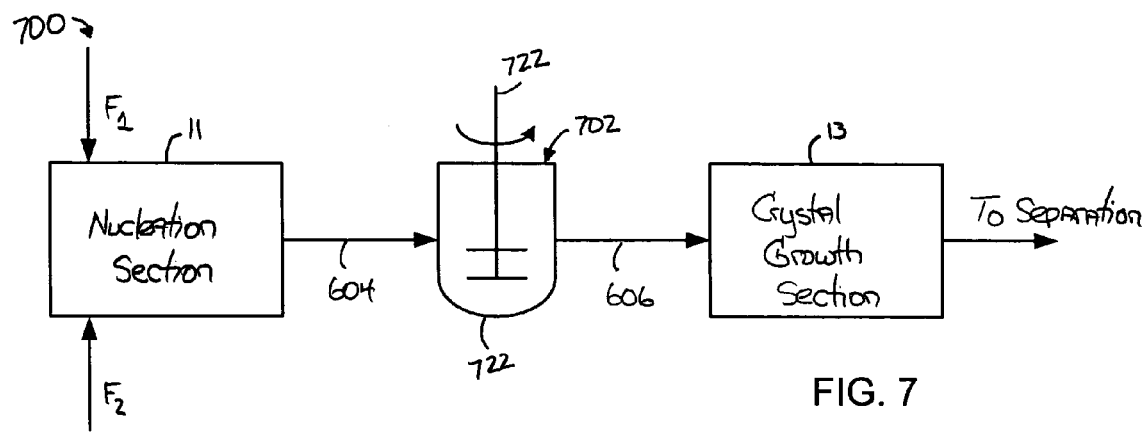
FIG. 7 is a flow diagram illustrating crystallization device 700 according to the present invention having an intermediate section 702, according to one embodiment of the present invention, that can be used in the device of FIG. 1.

Referring now to FIG. 7, FIG. 7 illustrates another embodiment of a crystallization device 700. Device 700 differs from device 600 of FIG. 6 in that intermediate section 702 comprises a combination of a tank 720 with a mixer 722 contained therein. Mixer 722 can be any suitable mixer (e.g., an electro-mechanical mixer, a magnetic stir bar mixer, etc.).

In operation, intermediate section 702 acts as a conduit that passes the fluid stream seed crystals formed in the one or more nucleating sections to one of the crystal growth section described in further detail below. In this embodiment, intermediate section 702 also acts to maintain the fluid nature of the fluid stream emitted from the one or more nucleation sections described above. This ensures that, in part, crystals do not form prematurely in the fluid stream as a result of the presence of the seed crystals contained in the fluid stream. Alternatively, or in addition to, the use of mixer 722 can suppress any premature increase in size of the seed crystals while in the fluid stream. (Oleg—Please confirm that this paragraph is accurate).

Figure 8:
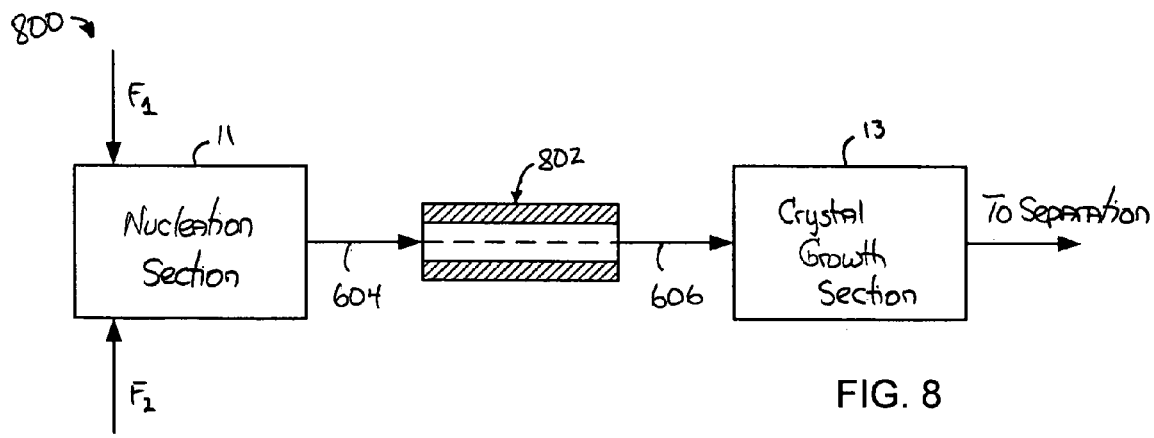
FIG. 8 is a flow diagram illustrating crystallization device 800 according to the present invention having an intermediate section 802, according to one embodiment of the present invention, that can be used in the device of FIG. 1.

Referring now to FIG. 8, FIG. 8 illustrates still another embodiment of a crystallization device 800. Device 800 differs from device 600 of FIG. 6 in that intermediate section 802 comprises a pipe or conduit that transfers the fluid stream and seed crystals emitted from the one or more nucleating sections to one of the crystal growth sections described below. Intermediate section 802 can be insulated and/or pressurized in order to maintain the physical and/or chemical conditions necessary to prevent premature crystallization of the compound in the fluid stream due to the presence of seed crystals.

Intermediate sections 602, 702 and/or 802 can de designed to permit the control of the pH of the fluid stream passing through the intermediate sections of the present invention. Control of the pH can be accomplished by introducing an appropriate pH controlled solution into intermediate sections 602, 702 and/or 802. Such solutions can include any suitable acid, base or neutral solution that can be used to accurately change the pH of the fluid stream in intermediate sections 602, 702 and/or 802.

Crystal Growth Sections:

The following text will discuss exemplary crystal growth sections 13 for use in crystallization device 10. Device 10 includes at least one crystal growth section 13. If more the one crystal growth section 13 is present in device 10, crystal growth sections 13 are connected in series.

Figure 9:
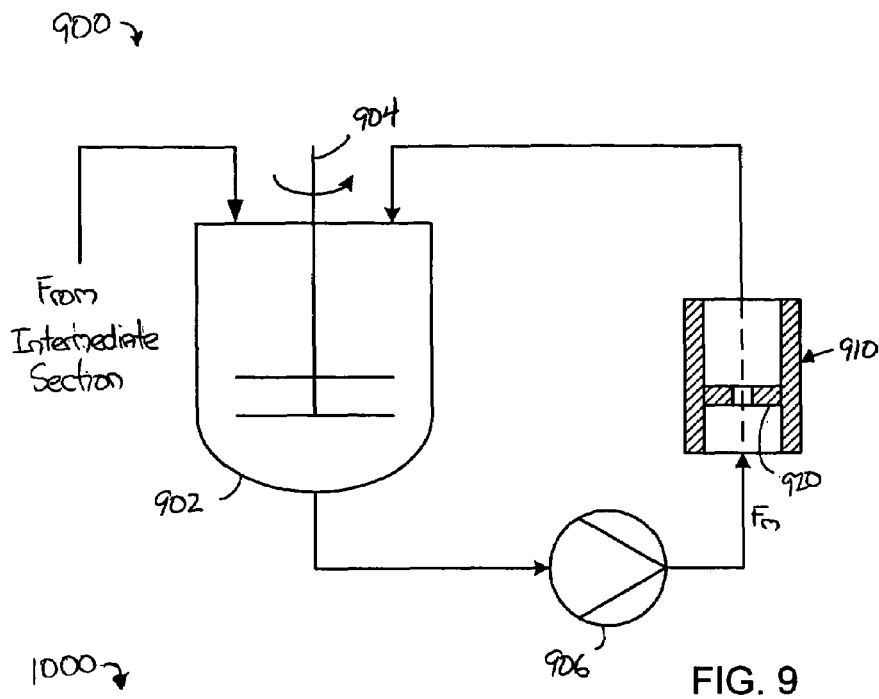
FIG. 9 is a cross-sectional diagram illustrating a crystal growth section 900, according to one embodiment of the present invention, that can be used in the device of FIG. 1.

Referring now to FIG. 9, FIG. 9 illustrates one embodiment of a crystal growth section 900. Section 900 comprises a combination of a tank 902 with a mixer 904 contained therein. Mixer 904 can be any suitable mixer (e.g., an electro-mechanical mixer, a magnetic stir bar mixer, etc.). Section 900 is connected via any suitable means (e.g., a pipe) to an intermediate section 12 of device 10. Tank 902 is connected via any suitable re-circulating means (e.g., a series of pipes) to a pump 906 and at least one hydrodynamic cavitation crystallization sub-section 910 that contains a cavitation generator 920. Cavitation generator 920 is identical in structure to cavitation generator 42 of FIG. 2. The type of pump used for pump 906 is determined on the basis of the physiochemical properties of the pumpable medium and the hydrodynamic parameters necessary for the accomplishment of the process.

Figure 10:
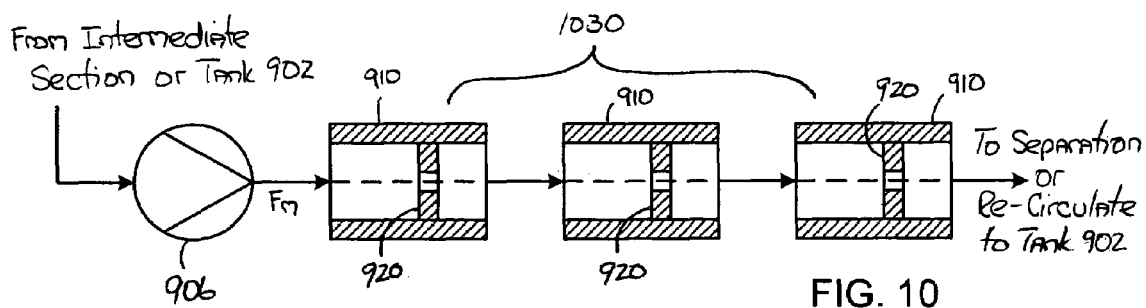
FIG. 10 is a cross-sectional diagram illustrating a crystal growth section 1000, according to one embodiment of the present invention, that can be used in the device of FIG. 1.

In the embodiment where more than one hydrodynamic cavitation crystallization sub-section is used in a crystal growth section 13 of device 10, the hydrodynamic cavitation crystallization sub-sections are connected in series to yield hydrodynamic cavitation crystallization sub-section 1030 of FIG. 10. The crystal growth sections described herein are not solely limited to re-circulating embodiments.

FIG. 10 illustrates a crystal growth section 1000 that can be used with or without the tank/mixer combination of FIG. 9. Hydrodynamic cavitation crystallization sub-section 1030 comprises at least three hydrodynamic cavitation crystallization sub-sections 910, each of which contains a cavitation generator cavitation generators 920. Sub-sections 910 are connected in series, and each of the cavitation generators 920 is identical in structure to the cavitation generator 42 of FIG. 2. As would be apparent to one of ordinary skill in the art, any one, or combination of cavitation generators, as disclosed in FIGS. 2 through 5, can be substituted for cavitation generators 920 of FIGS. 9 and 10. FIGS. 11A through 11D illustrate other embodiments of hydrodynamic cavitation crystallization sub-sections 910 that can be used in crystal growth sections of FIGS. 9 and/or 10.

Figure 11:
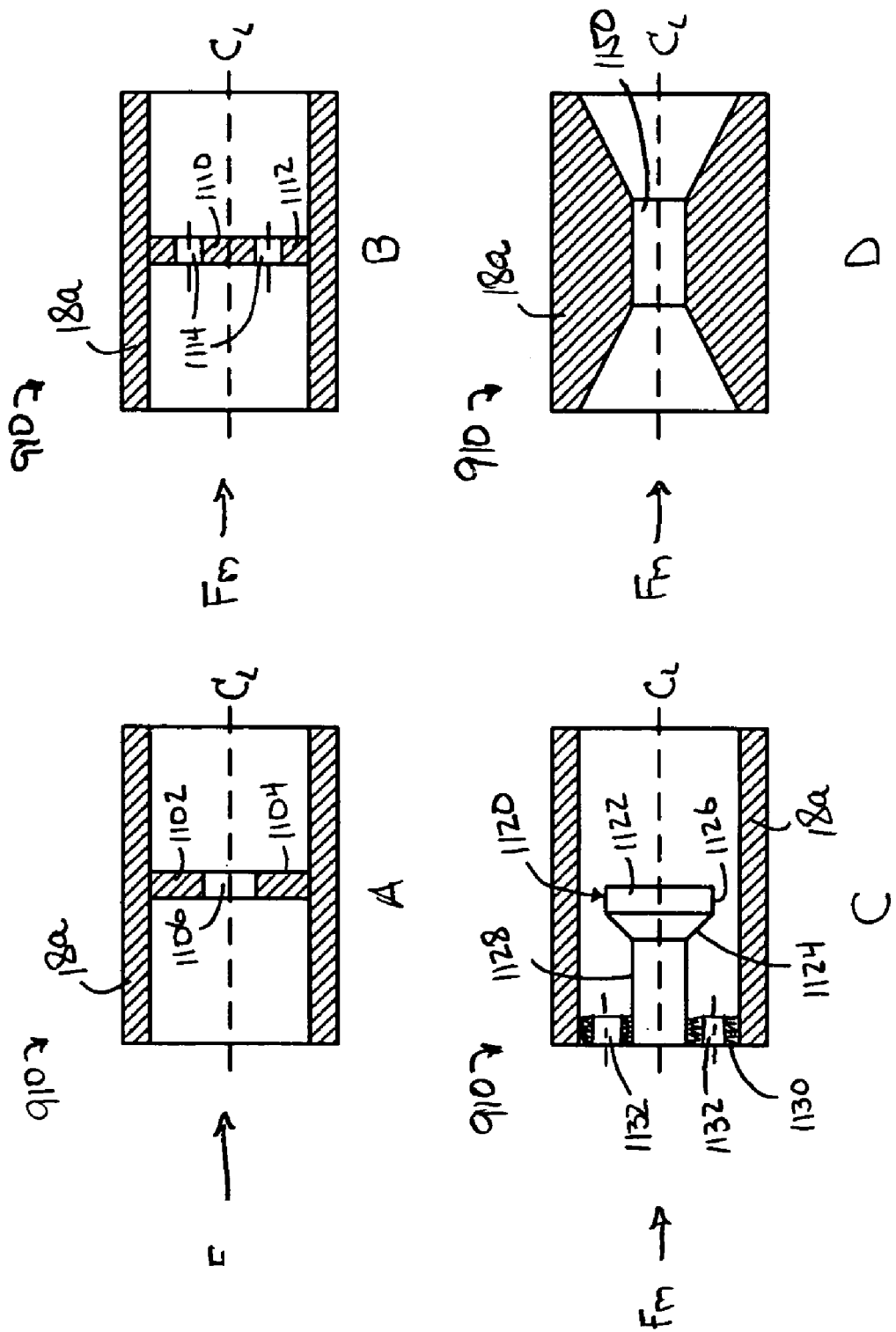
FIGS. 11A through 11D are cross-sectional diagrams illustrating crystal growth sections 2226a through 2226d, respectively, that can be used in the device of FIG. 1, or as the crystal growth section of FIGS. 9 and/or 10.

FIG. 11A illustrates a cavitation generator 1102 formed from a disk 1104 having a circular orifice 1106 disposed therein situated along or near the center line $C_L$ of flow-through channel 18a. Orifice 1106 is in the shape of Venturi tube and produces a local constriction of fluid flow. The sub-section of FIG. 11A differs from the ones disclosed in FIGS. 9 and 10 in that the diameter of orifice 1106 is larger.

FIG. 11B illustrates a cavitation generator 1110 formed from a disk 1112 having at least two circular orifices 1114 disposed therein. Orifices 1114 are in the shape of Venturi tubes and produce local constrictions of fluid flow. The cavitation generator 1110 of FIG. 11B operates in a manner similar to the cavitation generator of FIG. 11A except that cavitation generator 1110 utilizes at least two orifices to produce a minor loss of pressure in the fluid stream flowing through flow-through channel 18a.

FIG. 11C illustrates a cavitation generator 1120 formed from a baffle 1122. As shown in FIG. 11C, baffle 1122 includes a conically-shaped surface 1124 extending into a cylindrically-shaped surface 1126, wherein conically-shaped portion 1124 of baffle 1122 confronts the fluid flow. Baffle 1122 is positioned on a stem 1128 that is connected to disk 1130 having orifices 1132. Disk 1130 is mounted in flow-through channel 18a and retains baffle 1122 inside flow-through channel 18a. In place of disk 1130 having orifices 1132, it is possible to use a crosshead, post, propeller or any other fixture that produces a minor loss of pressure.

FIG. 11D illustrates a cavitation generator 1150 that is formed from a flow constriction in the walls of flow-through channel 18a. The constriction 1150 in flow-through 18a produces a minor loss in pressure.

While passing through the one or more flow constrictions present in the cavitation generators of the crystal growth sections described above, the velocity of the mixed fluid stream $F_m$ increases to a minimum velocity (i.e., velocity at which cavitation bubbles begin to appear) dictated by the physical properties of the mixed fluid stream $F_m$. As mixed fluid stream $F_m$ continues to pass through the one or more low constrictions contained in one of the crystal growth sections, a fixed hydrodynamic cavitation field generates cavitation bubbles downstream of the one or more flow constrictions. Upon reaching an elevated static pressure zone, the bubbles collapse causing high local pressures (up to 5,000 kg/cm$^2$) and/or shock waves, and temperatures (up to 15,000° C.) to effect crystallization in conjunction with the seed crystals present in the mixed fluid stream $F_m$ from the nucleating section of the crystallization device of the present invention. Fluid stream $F_m$ can be re-circulated to increase the concentration of crystals contained in mixed fluid $F_m$. Crystal size distribution can also be controlled by varying the pressure produced by the one or more cavitation generators and/or re-circulating mixed fluid stream $F_m$.

Crystal growth in one of the crystal growth sections described above can further be stimulated by subjecting fluid stream $F_m$ to conditions that momentarily alter the super-saturation gradient of the compound to be crystallized from fluid stream $F_m$.

After crystal growth has been completed, the crystals present in the fluid stream $F_m$ can be collected using any technique known in the art (e.g., filtration, evaporation, vacuum filtration, etc.).

Figure 12:
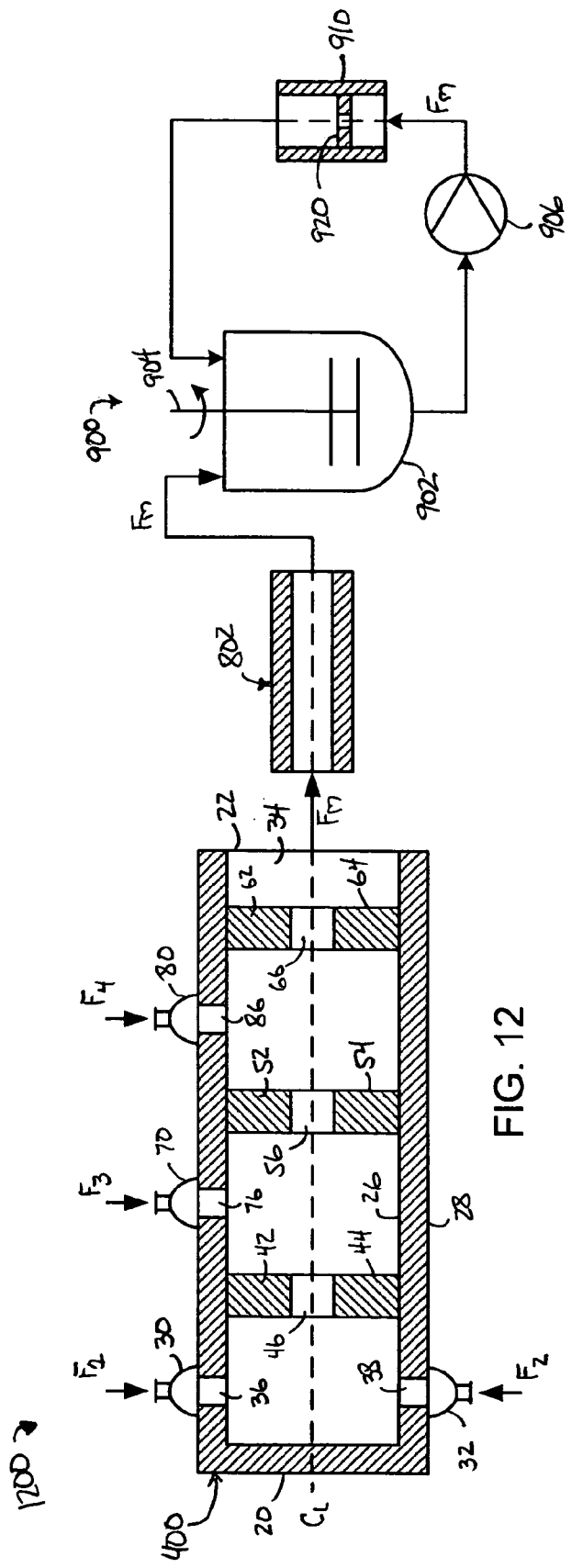
FIG. 12 is a cross-sectional diagram illustrating one example of a device according to FIG. 1 that includes the nucleation section of FIG. 4, the intermediate section of FIG. 8, and the crystal growth section of FIG. 9.

Exemplary Crystallization Device:

Referring now to FIG. 12, FIG. 12 illustrates one example of a crystallization device. Crystallization device 1200 includes the nucleation section 400 of FIG. 4, the intermediate section 802 of FIG. 8, and the crystal growth section 900 of FIG. 9. Device 1200 was used in the following examples. The examples are given for the purpose of illustrating the present invention and should not be construed as limitations on the scope or spirit of the instant invention.

EXAMPLE 1

Three p-acteylaminophenol (acetaminophen) solutions are prepared as follows: 23.888 grams of p-acteylaminophenol is added to 100 grams of 30:70 by weight water/EtOH solution. The crystallization process is carried out in the device of FIG. 12 where $F_1$, $F_3$, and $F_4$ are anti-solvent fluid streams and $F_2$ is a feed solution. The anti-solvent is water and is added via $F_1$, $F_3$, and $F_4$ to yield a final volume ratio of anti-solvent to feed solution of 70:30 when mixed fluid stream $F_m$ exits the nucleating section of device 1200. No additional heating, cooling or pH modification is conducted in intermediate section 802.

In the crystal growth section 900 of device 1200, mixed fluid stream $F_m$ is re-circulated via a high pressure pump through a hydrodynamic cavitation crystallization sub-section 910 containing cavitation generator 920.

The pressure of pump 906 is varied according to Table 1 and the re-circulation time is held constant at 5 minutes. At the end of the re-circulation time solution $F_m$ containing the desired crystals of p-acteylaminophenol are collected in a beaker and the crystal size distribution are examined with a LASENTEC instrument. The results are shown below in Table 1.

TABLE 1

| Pump Pressure (psi) | Crystal Sizes (microns) | | Final Volume Ratio (Anti-Solvent to Solvent) |
|---|---|---|---|
| | Number Weight Average | Square Weight Average | |
| 300 to 375 | 33 | 108 | 70:30 |
| 550 to 575 | 18 | 36 | 70:30 |
| 725 to 850 | 25 | 36 | 70:30 |

EXAMPLE 2

Two p-acteylaminophenol (acetaminophen) solutions are prepared as follows: 23.888 grams of p-acteylaminophenol is added to 100 grams of 30:70 by weight water/EtOH solution. The crystallization process is carried out in the device of FIG. 12 where $F_1$, $F_3$, and $F_4$ are anti-solvent fluid streams and $F_2$ is a feed solution. The anti-solvent is water and is added via $F_1$, $F_3$, and $F_4$ to yield a final volume ratio of anti-solvent to feed solution of 70:30 when mixed fluid stream $F_m$ exits the nucleating section of device 1200. No additional heating, cooling or pH modification is conducted in intermediate section 802.

In the crystal growth section 900 of device 1200, mixed fluid stream $F_m$ is re-circulated via a high pressure pump through a hydrodynamic cavitation crystallization sub-section 910 containing cavitation generator 920.

The pressure of pump 906 is varied according to Table 2 and the re-circulation time is held constant at 15 minutes. At the end of the re-circulation time solution $F_m$ containing the desired crystals of p-acteylaminophenol are collected in a beaker and the crystal size distribution are examined with a LASENTEC instrument. The results are shown below in Table 2.

TABLE 2

| Pump Pressure (psi) | Crystal Sizes (microns) | | Final Volume Ratio (Anti-Solvent to Solvent) |
|---|---|---|---|
| | Number Weight Average | Square Weight Average | |
| 400 to 500 | 35 | 100 | 70:30 |
| 750 to 925 | 15 | 30 | 70:30 |

EXAMPLE 3

Two p-acteylaminophenol (acetaminophen) solutions are prepared as follows: 23.888 grams of p-acteylaminophenol is added to 100 grams of 30:70 by weight water/EtOH solution. The crystallization process is carried out in the device of FIG. 12 where $F_1$, $F_3$, and $F_4$ are anti-solvent fluid streams and $F_2$ is a feed solution. The anti-solvent is water and is added via $F_1$, $F_3$, and $F_4$ to yield a final volume ratio of anti-solvent to feed solution of 70:30 when mixed fluid stream $F_m$ exits the nucleating section of device 1200. No additional heating, cooling or pH modification is conducted in intermediate section 802.

In the crystal growth section 900 of device 1200, mixed fluid stream $F_m$ is re-circulated via a high pressure pump through a hydrodynamic cavitation crystallization sub-section 910 containing cavitation generator 920.

The pressure of pump 906 is varied according to Table 3 and the re-circulation time is held constant at 30 minutes. At the end of the re-circulation time solution $F_m$ containing the desired crystals of p-acteylaminophenol are collected in a beaker and the crystal size distribution are examined with a LASENTEC instrument. The results are shown below in Table 3.

TABLE 3

| Pump Pressure (psi) | Crystal Sizes (microns) | | Final Volume Ratio (Anti-Solvent to Solvent) |
|---|---|---|---|
| | Number Weight Average | Square Weight Average | |
| 90 to 150 | 40 | 120 | 70:30 |
| 400 to 500 | 17 | 34 | 70:30 |

EXAMPLE 4

Three p-acteylaminophenol (acetaminophen) solutions are prepared as follows: 23.888 grams of p-acteylaminophenol is added to 100 grams of 30:70 by weight water/EtOH solution. The crystallization process is carried out in the device of FIG. 12 where $F_1$, $F_3$, and $F_4$ are anti-solvent fluid streams and $F_2$ is a feed solution. The anti-solvent is water and is added via $F_1$, $F_3$, and $F_4$ to yield a final volume ratio of anti-solvent to feed solution of 70:30 when mixed fluid stream $F_m$ exits the nucleating section of device 1200. No additional heating, cooling or pH modification is conducted in intermediate section 802.

In the crystal growth section 900 of device 1200, mixed fluid stream $F_m$ is re-circulated via a high pressure pump through a hydrodynamic cavitation crystallization sub-section 910 containing cavitation generator 920.

The pressure of pump 906 is held in the range of 400 to 500 psi and the re-circulation time is varied according to Table 4. At the end of the re-circulation time solution $F_m$ containing the desired crystals of p-acteylaminophenol are collected in a beaker and the crystal size distribution are examined with a LASENTEC instrument. The results are shown below in Table 4.

TABLE 4

| | Crystal Sizes (microns) | | Final Volume Ratio |
|---|---|---|---|
| Re-Circulation Time (minutes) | Number Weight Average | Square Weight Average | (Anti-Solvent to Solvent) |
| 15 | 35 | 100 | 70:30 |
| 20 | 26 | 50 | 70:30 |
| 30 | 17 | 34 | 70:30 |

EXAMPLE 5

A p-acteylaminophenol (acetaminophen) solution is prepared as follows: 20.976 grams of p-acteylaminophenol is added to 100 grams of 30:70 by weight water/EtOH solution. The crystallization process is carried out in the device of FIG. 12 where $F_1$, $F_3$, and $F_4$ are anti-solvent fluid streams and $F_2$ is a feed solution. The anti-solvent is water and is added via $F_1$, $F_3$, and $F_4$ to yield a final volume ratio of anti-solvent to feed solution of 70:30 when mixed fluid stream $F_m$ exits the nucleating section of device 1200. No additional heating, cooling or pH modification is conducted in intermediate section 802.

In the crystal growth section 900 of device 1200, mixed fluid stream $F_m$ is re-circulated via a high pressure pump through a hydrodynamic cavitation crystallization sub-section 910 containing cavitation generator 920.

The pressure of pump 906 is 6,800 psi and solution $F_m$ is re-circulated 5 times through crystal growth section 900. At the end of re-circulation, solution $F_m$ containing the desired crystals of p-acteylaminophenol are collected in a beaker and the crystal size is analyzed with a HORIBA instrument. The mean particle size is 5 microns.

While the present application illustrates various embodiments, and while these embodiments have been described in some detail, it is not the intention of the applicant to restrict or in any way limit the scope of the claimed invention to such detail. Additional advantages and modifications will readily appear to those skilled in the art. Therefore, the invention, in its broader aspects, is not limited to the specific details, the representative apparatus, and illustrative examples shown and described. Accordingly, departures may be made from such details without departing from the spirit or scope of the applicant's claimed invention.

What is claimed is:

1. A process for crystallizing a compound using hydrodynamic cavitation, the method comprising:
colliding at least one stream of a solution of such compound to be crystallized against at least one stream of an anti-solvent in a nucleating section of a crystallization device to create a transient cavitation field, thereby yielding a mixed fluid stream and seed crystals;
passing the mixed fluid stream and seed crystals at an elevated pressure through at least one local constriction of flow to create a fixed hydrodynamic cavitation field in the nucleation section, thereby yielding a mixed fluid stream and additional and/or larger seed crystals;
passing the mixed fluid stream containing the seed crystals through an intermediate section of the crystallization devices,
passing the mixed fluid stream containing the seed crystals through a crystal growth section of the crystallization device comprising at least one local constriction of flow to create hydrodynamic cavitation, thereby causing further crystallization or crystal growth of the seed crystals contained in the mixed fluid stream.

2. The process of claim 1, wherein the compound to be crystallized is an inorganic material.

3. The process of claim 1, wherein the compound to be crystallized is an organic material.

4. The process of claim 1, wherein the nucleating comprises two or more local constrictions of flow.

5. The process of claim 4, wherein additional anti-solvent fluid streams are supplied between adjacent local constrictions of flow.

6. The process of claim 1, wherein the temperature and/or pH of the fluid stream is modified in the intermediate section.

7. The process of claim 6, wherein the temperature of the fluid stream is modified in the intermediate section via at least one heat exchanger.

8. The process of claim 1, wherein the crystal growth section comprises two or more local constrictions of flow.

9. The process of claim 1, wherein the size distribution of the crystals produced in the crystal growth section is determined by controlling the pressure of the fluid stream in the crystal growth section.

10. The process of claim 1, wherein the crystal growth section further comprises a fluid re-circulating means.

11. The process of claim 10, wherein the size distribution of the crystals produced in the crystal growth section is determined by the re-circulation time of the fluid stream in the crystal growth section.

12. The process of claim 1, further comprising the step of adding at least one compound to the mixed fluid stream in either one or all of the nucleating, intermediate and/or crystal growth sections, wherein the at least one compound is selected from a surfactant, a stabilizer, a crystal growth promoting compound, or mixtures of two or more thereof.

13. A device for crystallizing a compound using hydrodynamic cavitation comprising:
at least one nucleating section, the nucleating section having one open end to permit the passage of a fluid stream out of the nucleating section, the nucleating section including:
(i) a flow channel having an anti-solvent inlet and a feed solution inlet, the inlets being designed to introduce an anti-solvent and a feed solution into the flow channel, the inlets being located opposite one another in order to permit the anti-solvent fluid stream and the feed solution fluid stream to collide with one another upon entry into the flow channel to create a transient cavitation field, thereby yielding a mixed fluid stream and seed crystals;
  (ii) at least one fixed cavitation generator positioned in the flow channel at a position downstream of the transient cavitation field, the fixed cavitation generator providing at least one local constriction of flow designed to cause hydrodynamic cavitation to effectuate nucleation and produce additional and/or larger seed crystals in the mixed fluid stream;
at least one intermediate section having an input and an output, the input being connected via a suitable connection means to the open end of the nucleating section so as to receive the mixed fluid stream and seed crystals from the nucleating section; and
a crystal growth section having an input for receiving the mixed fluid stream and seed crystals from the output of the intermediate section, the crystal growth section comprising at least one hydrodynamic cavitation subsection having at least one local constriction of flow.

14. The device of claim 13, wherein the flow channel of the nucleating section has a substantially circular cross-section.

15. The device of claim 13, wherein the nucleating includes two or more local constrictions of flow.

16. The device of claim 15, wherein additional inlets are located in the flow channel of the nucleating section to provide additional anti-solvent between adjacent local constrictions of flow.

17. The device of claim 13, wherein the intermediate section includes at least one heat exchanger, mixer, or combination thereof.

18. The device of claim 13, wherein the temperature and/or pH of the fluid stream is modified in the intermediate section.

19. The device of claim 13, wherein the crystal growth section includes two or more local constrictions of flow.

20. The device of claim 13, wherein the crystal growth section further includes a fluid re-circulating means.

21. The device of claim 13, further comprising input means for inputting at least one compound to the mixed fluid stream in either one or all of the nucleating, intermediate and/or crystal growth sections, wherein the at least one compound is selected from a surfactant, a stabilizer, a crystal growth promoting compound, or mixtures of two or more thereof.

* * * * *